US010713973B2

(12) United States Patent
Kuwabara et al.

(10) Patent No.: US 10,713,973 B2
(45) Date of Patent: Jul. 14, 2020

(54) MODEL OF VISCERA, TISSUES, OR ORGANS

(71) Applicants: SUNARROW LTD, Tokyo (JP); Niigata University, Niigata (JP)

(72) Inventors: Yutaka Kuwabara, Niigata (JP); Atsushi Ogawa, Niigata (JP); Ken-ichi Mizuno, Niigata (JP); Hiroki Sato, Niigata (JP); Shuji Terai, Niigata (JP)

(73) Assignees: SUNARROW LTD, Tokyo (JP); NIIGATA UNIVERSITY, Niigata (JP)

( * ) Notice: Subject to any disclaimer, the term of this patent is extended or adjusted under 35 U.S.C. 154(b) by 260 days.

(21) Appl. No.: 16/060,866

(22) PCT Filed: Dec. 2, 2016

(86) PCT No.: PCT/JP2016/085945
§ 371 (c)(1),
(2) Date: Jun. 8, 2018

(87) PCT Pub. No.: WO2017/099023
PCT Pub. Date: Jun. 15, 2017

(65) Prior Publication Data
US 2018/0357930 A1  Dec. 13, 2018

(30) Foreign Application Priority Data
Dec. 10, 2015 (JP) ................. 2015-241410

(51) Int. Cl.
G09B 23/30 (2006.01)
G09B 23/28 (2006.01)
A61L 27/52 (2006.01)
G09B 23/00 (2006.01)

(52) U.S. Cl.
CPC ............ *G09B 23/285* (2013.01); *A61L 27/52* (2013.01); *G09B 23/00* (2013.01); *G09B 23/28* (2013.01); *G09B 23/30* (2013.01)

(58) Field of Classification Search
None
See application file for complete search history.

(56) References Cited

U.S. PATENT DOCUMENTS

| 6,474,993 | B1 | 11/2002 | Grund et al. |
| 6,608,117 | B1 | 8/2003 | Gvozdic |
| 2002/0076681 | A1* | 6/2002 | Leight .................... G09B 23/30 434/273 |
| 2004/0224021 | A1 | 11/2004 | Omidian et al. |

(Continued)

FOREIGN PATENT DOCUMENTS

| JP | 2010/277003 A | 12/2010 |
| JP | 2013-015789 A | 1/2013 |

(Continued)

OTHER PUBLICATIONS

International Preliminary Report on Patentability issued in PCT/JP2016/085945 dated Jun. 21, 2018 (6 pages).

(Continued)

*Primary Examiner* — Jason T Yen
(74) *Attorney, Agent, or Firm* — Osha Liang LLP

(57) ABSTRACT

Provided is a pseudo visceral model having a specific texture.
A model of viscera, tissues, or organs comprising a foam layer containing a hydrogel.

13 Claims, 9 Drawing Sheets

(56) References Cited

U.S. PATENT DOCUMENTS

| | | | |
|---|---|---|---|
| 2009/0254179 A1* | 10/2009 | Burnett | A61B 5/6846 623/8 |
| 2011/0207103 A1* | 8/2011 | Trotta | B29C 39/021 434/267 |
| 2012/0045743 A1 | 2/2012 | Okano et al. | |
| 2012/0282584 A1 | 11/2012 | Millon et al. | |
| 2014/0248596 A1* | 9/2014 | Hart | G09B 23/30 434/272 |
| 2016/0372010 A1 | 12/2016 | Hokazono | |
| 2017/0186340 A1 | 6/2017 | Ogawa et al. | |
| 2017/0239886 A1 | 8/2017 | Norikane | |

FOREIGN PATENT DOCUMENTS

| | | |
|---|---|---|
| JP | 2015-138192 A | 7/2015 |
| JP | 5759055 B1 | 8/2015 |
| JP | 2015-194708 A | 11/2015 |
| JP | 2016/085945 A | 2/2017 |
| WO | 98/25254 A1 | 6/1998 |
| WO | 2011/035410 A1 | 3/2011 |

OTHER PUBLICATIONS

International Search Report issued in PCT/JP2016/085945 dated Feb. 28, 2017 (5 pages).
Written Opinion issued in PCT/JP2016/085945 dated Feb. 28, 2017 (4 pages).

* cited by examiner

II-II

MODEL OF VISCERA, TISSUES, OR ORGANS

TECHNICAL FIELD

The present invention relates to a model having a visceral or tissular texture (a pseudo visceral model) in which the texture of a real object (real viscus) is replicated realistically.

BACKGROUND ART

In the related art, viscera and tissues of animals and body donations (human corpses) have been used for simulations of medical practice. However, viscera and tissues of animals used in the related art are different from actual viscera and tissues of living human beings in shape, size, and texture. In addition, using animals' viscera and tissues leads to higher costs and raises an ethical problem. Furthermore, when a busy doctor runs a simulation outside the operating room in his/her free time, it is not preferable to use animals' viscera and the like from a view point of hygiene and indoor conditions.

Therefore, there is a demand for pseudo visceral models suitable for simulations of medical practice. It is important that pseudo visceral models are virtual models (pseudo viscera) that are identified as real objects (real viscera). An achievement of virtual models identified as real objects (real viscera) contributes to an improvement in surgical techniques.

Furthermore, in recent years, various types of surgeries have been researched and developed, and it is required to impart visceral models with characteristics and properties resembling more closely to real objects (real viscera).

For example, Patent Literature 1 proposes a molded article made of a soft material.

CITATION LIST

Patent Literature

Patent Literature 1: JP 2013-015789 A

SUMMARY OF INVENTION

Technical Problem

In surgical simulations, what is more necessary for pseudo (simulated) visceral models is to impart them with properties and characteristics such as those possessed by actual viscera than to give color or appearance of the actual viscera.

For example, it is important that visceral models have degree of replication (a sense of dissection: for example, a feeling of ripping tissues while stretching the tissues, or a feeling of pushing aside cells and tissues) in dissection, division, incision, or resection of peritonea, fat layers, stratum disjunctum, and the like which are peripheral tissues obstructing an operative field or surrounding a viscus.

From such a viewpoint, the invention according to Patent Literature 1 does not provide sufficient degree of replication in regard to unique texture and feeling, such as a sense of dissection, required for visceral models.

The present invention has been made in light of the above problem, and an object of the present invention is to provide a pseudo visceral model (pseudo tissular model, or pseudo organic model) imparted with a specific texture which is usable for simulations (learning, training, practice, proficiency, drill, and the like) in medical practice such as surgery, tissue diagnosis (biopsy), cytological diagnosis, and pathological anatomy and which is effective for development in medical equipment. More specifically, an object of the present invention is to provide a pseudo visceral model (a pseudo tissular model, or a pseudo organic model) which has a specific texture (particularly, a sense of dissection) and which is applicable to various types of surgical simulations.

Solution to Problem

The inventors of the present invention have studied intensively and found that the aforementioned problem is solvable by employing a gel layer having a specific structure as a layer structure of a visceral model. In other words, the present invention is as follows.

The present invention (1) is a model of viscera, tissues, or organs comprising a foam layer containing a hydrogel.

The present invention (2) is the model of viscera, tissues, or organs according to the invention (1), wherein the model is a laminate in which another layer is laminated on one surface of the foam layer.

The present invention (3) is the model of viscera, tissues, or organs according to the invention (2), wherein the model is a laminate in which another layer is laminated on the other surface of the foam layer.

The present invention (4) is the model of viscera, tissues, or organs according to any one of the inventions (1) to (3), wherein the foam layer contains a polysaccharide.

The present invention (5) is the model of viscera, tissues, or organs according to any one of the inventions (1) to (4), wherein the hydrogel is a polyvinyl alcohol gel.

The present invention (6) is the model of viscera, tissues, or organs according to any one of the inventions (1) to (5), wherein the model is for a simulation of dissection.

The present invention (7) is the model of viscera, tissues, or organs according to any one of the inventions (1) to (6), wherein the model is for a simulation of localized injection.

The present invention (8) is the model of viscera, tissues, or organs according to any one of the inventions (1) to (7), wherein the model is for incision and/or dissection with an energy device.

Advantageous Effects of Invention

According to the present invention, it is possible to provide a pseudo visceral model having various properties including a specific texture (particularly, a sense of dissection) which is usable for simulations in medical practice and effective for development in medical equipment.

DESCRIPTION OF EMBODIMENTS

A model of viscera, tissues, or organs (hereinafter simply referred to as the "visceral model" and the like) according to the present invention includes a foam layer containing a hydrogel. In a visceral model, a layer with a hydrogel having a foam structure creates a specific texture (in other words, the present invention employs a foam layer containing a hydrogel as at least one layer included in a visceral model so as to improve the texture of the visceral model).

A specific embodiment of the visceral model according to the present invention will hereinafter be described in detail in the following order, but the present invention is not limited to the embodiment. In the following description, for example, the foam layer included in the visceral model is formed in a plate-like shape or tubular (hollow or solid) shape, but the present invention is not limited thereto, and the foam layer may be appropriately formed in a shape resembling viscera, organs, and tissues of interest. More specifically, the visceral model according to the present invention may have the foam layer (a part having the foam structure), and the shape of the foam layer may be appropriately changed depending on the intended use (for example, the foam layer may be a lump, or each layer may have distortion or irregularities). Furthermore, the thickness and length of the entire laminate as well as the thickness and length of each layer may be changed appropriately depending on the intended use (for example, the laminate may include a sheet-like or film-like layer).

(1) Embodiment
(1-1) Structure
(1-2) Production method
(1-3) Properties
(1-4) Use
(2) Modification
(2-1) Structure
(2-2) Production method Note that an embodiment and a modification thereof should not be limitedly understood that they are applicable to specific ones and may be applicable to any combinations. For example, it should be understood that a modification of a certain embodiment may be a modification of another embodiment. Furthermore, even when a certain embodiment and another embodiment (or a certain modification and another modification) are described independently, it should be understood that those embodiments (modifications) may be combined.

Embodiment

A visceral model according to the present embodiment (hereinafter referred to as a "visceral model A101") includes a foam layer having a plate-like shape. Hereinafter, the structure, production method, properties, and use of the visceral model A101 will be described.

<Structure>

The visceral model A101 includes a laminate in which a plurality of layers is laminated.

Figure 1A:
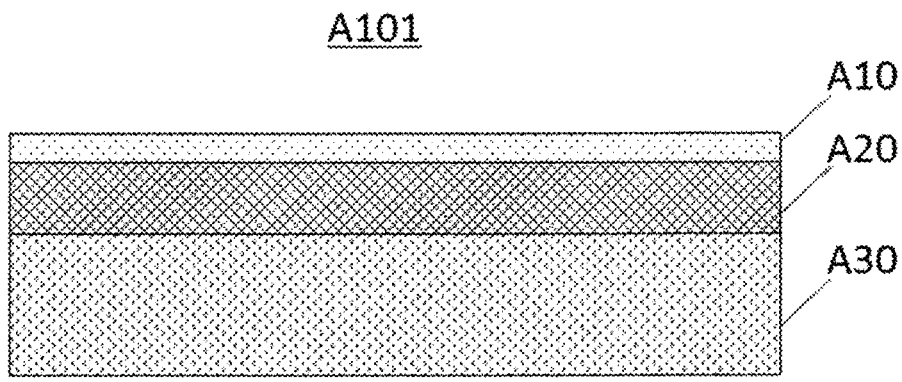
FIGS. 1A to 1C illustrate conceptual diagrams of a visceral model A101 according to the present embodiment.
Figure 1B:
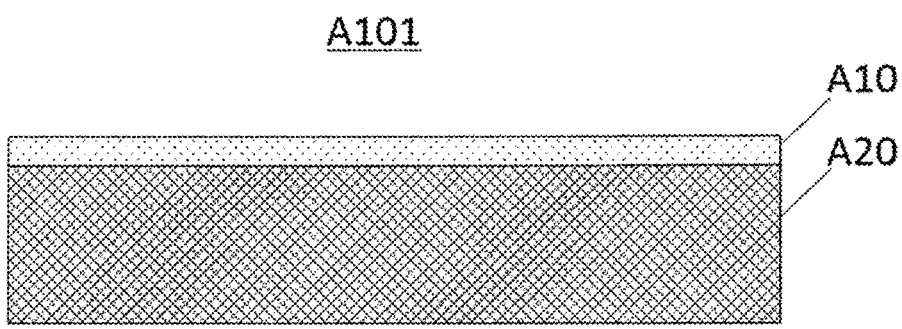
Figure 1C:
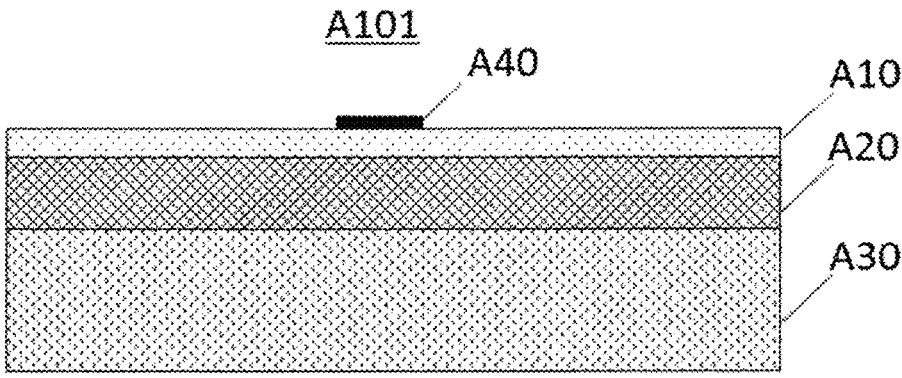

More specifically, as illustrated in FIG. 1A, the visceral model A101 has a laminate structure including a second layer A20 which is a foam layer (hereinafter referred to as a "foam layer A20"); a third layer A30 provided on one surface of the second layer A20; and a first layer A10 provided on the other surface of the second layer A20. Hereinafter, the visceral model A101 will be illustrated as having such a three-layer structure, but the present invention is not limited thereto. The layer structure may be changed appropriately depending on the intended use. For example, the visceral model A101 may have a single-layer structure including the foam layer A20, or may have a double-layer structure including the foam layer A20 and the first layer A10 provided on one surface of the foam layer A20 as illustrated in FIG. 1B (in FIG. 1B, the first layer A10 is provided as a superficial layer, but the foam layer A20 may be provided as a superficial layer). Alternatively, the visceral model A101 may have a laminate structure including four layers or more. Such a structure is illustrated in FIG. 1C, including, for example, the first layer A10, the foam layer A20, the third layer A30, and a fourth layer A40 (as illustrated, the structure may include a foreign matter that resembles a tumor). Furthermore, in the visceral model A101, a plurality of foam layers A20 may be laminated, and the order of the lamination may be changed appropriately (for example, foam layers and non-foam layers may be laminated alternately like non-foam layer/foam layer/non-foam layer/foam layer/non-foam layer, or foam layers may be laminated continuously like foam layer/foam layer/non-foam layer, or foam layers may be laminated without non-foam layers like foam layer/foam layer/foam layer).

(Foam Layer)

The foam layer A20 of the visceral model A101 according to this embodiment is a foam layer containing a hydrogel, more specifically, a layer having a foam structure obtained by foaming a material that contains a hydrogel.

Foam Structure

With regard to the foam structure of the foam layer A20 according to this embodiment, specific examples include an open-cell foam structure, and a closed-cell foam structure. The foam structure may include both of these structures.

A foaming ratio of the foam layer A20 is not particularly limited and may be changed appropriately depending on the intended use, but a foaming ratio is preferably 1.1 to 10.0 times, and more preferably 1.5 to 5.0 times. The foaming ratio thereof is a numerical value represented by the density of the material (before foaming)/the bulk density of the foam layer (after foaming).

Furthermore, the foam layer A20 may have such a structure that some parts are foamed, and the other parts are not foamed (a structure in which a foam portion and a non-foam portion continuously exist in the layer) as long as a part used in a surgery (for example, a part to be incised) has a foam structure.

Material

A material of the hydrogel used for the foam layer A20 is not particularly limited, but it is preferable to use a polymer gel material such as polyvinyl alcohols, polyethylene glycols, and polyacrylamides, or a natural gel material such as cellulose, starch, and collagen (the foam layer A20 may contain many different types of hydrogel). These gels may be modified at least partially (for example, polyvinyl alcohols may be modified polyvinyl alcohols (anionic-modified polyvinyl alcohols, cationic-modified polyvinyl alcohols, and nonionic-modified polyvinyl alcohols)). To solve the problem of the present invention, it is particularly preferable that the hydrogel is a polyvinyl alcohol (polyvinyl alcohol gel) (or that the hydrogel contains a polyvinyl alcohol as a main component).

When the foam layer A20 includes a polyvinyl alcohol as the hydrogel, a mean degree of polymerization of the polyvinyl alcohol is not limited but is preferably 500 to 3000, more preferably 1000 to 2000, and still more preferably 1500 to 2000. A degree of saponification of polyvinyl alcohol is not limited but is preferably 90 mol % or more, and more preferably 95 mol % or more. In a case of compounding plural kinds of polyvinyl alcohols having different degrees of polymerization, for example, the mean degree of polymerization represents the mean degree of polymerization of these plural kinds of polyvinyl alcohols (mean degree of polymerization and degree of saponification may be numerical values measured in accordance with JIS K 6726, using one or plural kinds of polyvinyl alcohols as a sample(s)).

With regard to cross-linking form, the hydrogel may not be cross-linked, but it is preferable that the hydrogel is cross-linked (physically cross-linked (physical gel) or chemically cross-linked (chemical gel)). A specific method of cross-linking is not limited, and a known method may be employable, including selection of a cross-linking agent (for example, a cross-linking agent which is usable when a polyvinyl alcohol is included as a hydrogel is not particularly limited, and an example of the cross-linking agent includes an agent capable of reacting with a hydroxyl group in the polyvinyl alcohol (for example, boric acid and the like)).

The water content of the hydrogel (the water content in the foam layer A20) is not particularly limited but is preferably, for example, 50 mass % or more, and more preferably 70 mass % or more with respect to the entire foam layer. Such water content enables a more realistic texture.

The foam layer A20 may further contain other appropriate additives depending on the intended use. For example, a coloring agent (for example, an agent that applies colors resembling human tissues or blood) may be added to the hydrogel material depending on the intended use. Coloring with the coloring agent makes it possible to color the visceral model as similar to the viscera of a human body (or makes it possible to visually distinguish each layer). Other known additives (such as antioxidants, and thickeners) may also be added.

Furthermore, the foam layer A20 may contain a solid filler such as a filler or fibers (such as cotton, linen, and wool).

It is preferable that the foam layer A20 contains a polysaccharide (one or plural kinds of polysaccharides may be included). Compounding a polysaccharide in the foam layer A20 improves the texture of the visceral model. The polysaccharide used herein is not particularly limited and a known polysaccharide may be used appropriately. Examples of the polysaccharide include agarose, amylose, amylopectin, arabinan, alginic acid, inulin, carrageenan, galactan, galactomannan, carboxymethylcellulose, agar, xanthan gum, xylan, chitin, chitosan glucomannan, chondroitin sulfate, gellan gum, cellulose, dextrin, hyaluronic acid, fucoidan, pullulan, pectic acid, heparin, mannan, and salts and derivatives of these polysaccharides.

The amount of such additives (for example, polysaccharides) to be compounded is not particularly limited and may be appropriately set within the range not hindering the effects of the invention. For example, when the polysaccharide is compounded in the foam layer A20, the amount may be set to 0.1 to 50.0 mass % with respect to the mass of the entire layer (the mass of the whole material).

(Other Layers)

The visceral model A101 has other layers on one surface and the other surface of the foam layer A20 (the superficial layer (layer on upper side) is defined as the first layer A10, and the deeper layer (layer on the lower side) is defined as the third layer A30).

In such a manner, as the visceral model A101 is appropriately configured to have a laminate structure, the visceral model A101 corresponds to a layer structure of viscera of interest (including tissues and organs), and it is possible to replicate a more realistic texture in the visceral model. For example, when the visceral model A101 is configured to have a three-layer structure, it is possible to replicate a more realistic viscus having three layers (for example, a gastric model including a mucosa layer, a submucosa layer, and a muscle layer).

Furthermore, in using the visceral model A101 for localized injection (for a simulation of localized injection), providing the visceral model A101 with the third layer A30 as a layer adjacent to the second layer A20 makes it easier to hold liquid at the time of localized injection.

Such layers (other layers) may be made of a material similar to that of the foam layer A20 or may be made of a different material. Furthermore, other layers may be made of a hydrogel material, or a soft material other than a hydrogel material. Alternatively, other layers may include a hard material (or may be made of a hard material).

<Production Method>

A production method of the visceral model A101 is not limited to the following method, and the visceral model A101 may be produced by any appropriate method. For example, the visceral model A101 having the first layer A10, second layer A20 (foam layer A20), and third layer A30 made of a hydrogel material can be produced by the following procedure. The first and third layers A10 and A30 can be produced in accordance with a production method of the foam layer A20, except that those layers are produced by skipping the step of foaming. Therefore, the production method of the first and third layers A10 and A30 will not be described below.

Foam Layer A20

The foam layer A20 may be produced in accordance with a known production method except that the production method of the foam layer A20 includes the step of foaming. A specific example will hereinafter be described. Examples of the specific material are described above and will not be described below.

Figure 2A:
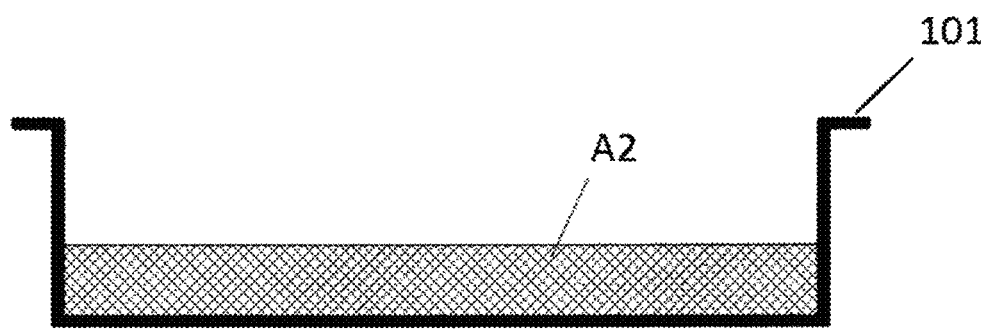
FIGS. 2A and 2B illustrate conceptual diagrams of a production method of the visceral model A101 according to the present embodiment.
Figure 2B:

First, a material included in the hydrogel material is compounded, stirred and dissolved while being heated so as to obtain a mixture (heating conditions are not limited, but it is preferable to heat the material, for example, at 60 to 100° C. for 1 hour or more, and more preferably, for 3 hours or more). In addition, the material (additives and the like) is appropriately mixed and stirred in the mixture so as to prepare a material composition (the step of preparing material). It should be noted that preparation of the mixture and preparation of the material composition may be carried out simultaneously. Subsequently, the material composition is foamed to obtain a foam material A2 (the step of foaming). Next, the foam material A2 which is foamed to contain air bubbles is poured into a tray 101 or the like (FIG. 2A) and allowed to stand and cured (the step of curing) so as to yield a foam layer A20 (FIG. 2B).

When various types of additives are used, the additives may be added at any time, but it is preferable to add before the step of foaming.

It is preferable to perform curing with a cross-linking agent (cross-linking) from a viewpoint that the cross-linking agent accelerates curing while maintaining the state of foaming. When using a cross-linking agent, the cross-linking agent may be added at any time, before the step of foaming or after the step of foaming (when it is difficult to mix an additive after the step of foaming, the additive may be mixed in the material composition before the step of foaming).

When a cross-linking agent is not used, a possible embodiment as the step of curing is such that the foam material A2 is frozen and thawed (for example, the foam material A2 is froze at the temperature of −5° C. or less for 0.5 hours or more) so that the hydrogel crosslinks physically. It should be noted that the step of chemical cross-linking and the step of physical cross-linking may be carried out together.

As a specific foaming method, a known method including chemical foaming, physical foaming, and mechanical foaming may be employed appropriately. Furthermore, the specific conditions of foaming (for example, the stirring speed, and air to be used in mechanical foaming) are not particularly limited and may be set appropriately within the range not hindering the effect of the present invention.

It is preferable that the material composition (or the foam material A2) contains a polysaccharide as an additive. In this case, the polysaccharide functions as a thickener and makes it easy to maintain the state of foaming in the step of curing.

Lamination

Figure 3A:
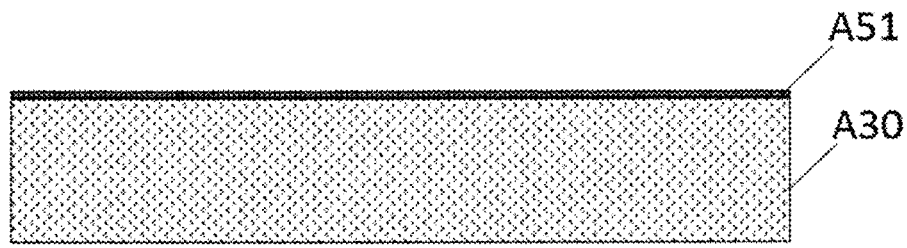
FIGS. 3A to 3C illustrate conceptual diagrams of the production method of the visceral model A101 according to the present embodiment.
Figure 3B:
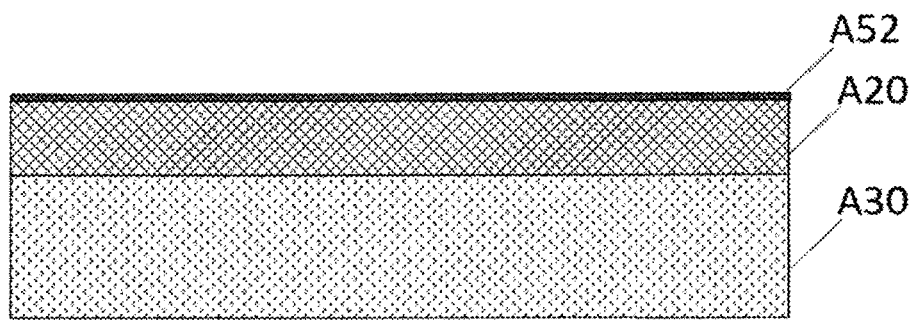
Figure 3C:
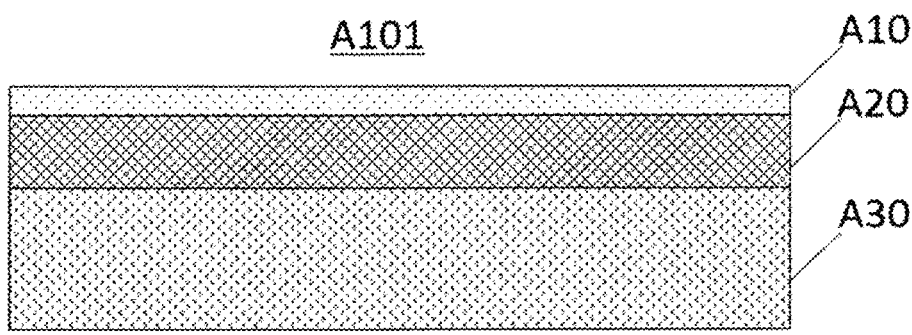

Next, as illustrated in FIGS. 3A to 3C, the first layer A10, foam layer A20, and third layer A30 are appropriately laminated and fixed to each other with an adhesive A51 (adhesive A52) and the like.

Such an adhesive (adhesive layer) is not particularly limited and may be appropriately selected within the range not hindering the effect of the present invention. For example, when the first layer A10 (third layer A30) contains a hydrogel, a material including a hydrogel may be used as the adhesive.

Alternatively, another layer may be directly (without an adhesive or the like) laminated and solidified to an unsolidified layer (a layer containing a hydrogel) so that the layers are bonded to each other.

Even when a layer other than the hydrogel-containing layer is used as the first and third layers and the like to form a visceral model, any appropriate methods as described above, in which layers are adhered to each other, enables production of the visceral model.

Figure 4A:
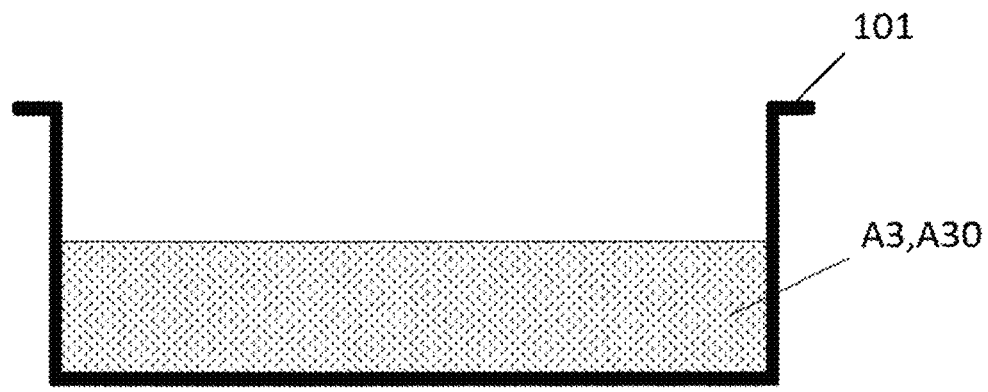
FIGS. 4A to 4C illustrate conceptual diagrams of the production method of the visceral model A101 according to the present embodiment.
Figure 4B:
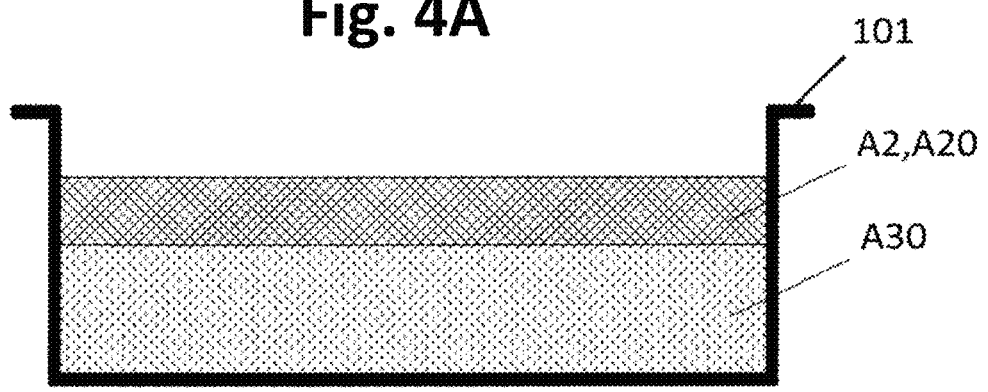
Figure 4C:
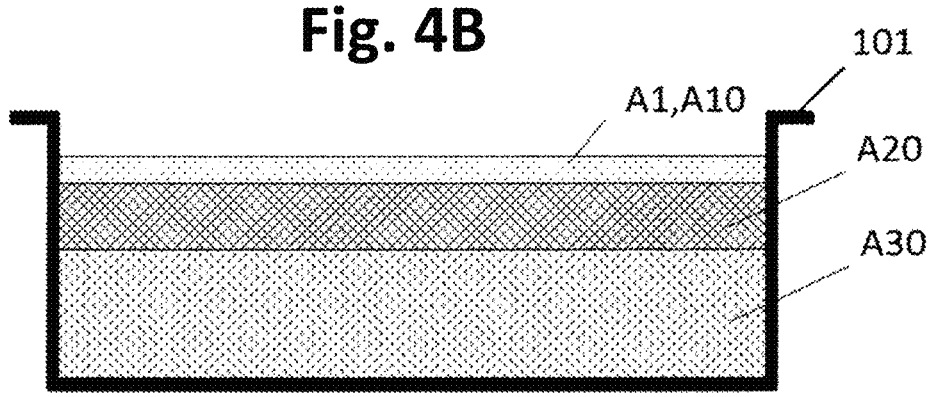

As another example of the production method of the visceral model A101, as illustrated in FIG. 4, a third layer-material liquid A3 is poured into the tray 101 and cured to form the third layer A30 (FIG. 4A), and then, the foam material A2 is poured from above the third layer A30 and cured to form the second layer A20 (the foam layer A20) (FIG. 4B), and finally, a first layer material A1 is poured from above the foam layer A20 and cured to form the first layer A10 (FIG. 4C). Such a method enables appropriate lamination and fixation of layers (the first layer A10, foam layer A20, and third layer A30) without adhesive layers (the adhesive A51, and adhesive A52).

Similarly, in a case of laminating a thin layer (for example, a sheet-like or film-like layer), the production method of the visceral model A101 may be such that a material composition (or a foam material) of another layer is applied to (coated on) a certain layer and fixed.

As a method of fixing layers, other methods such as physical fixing (for example, fixing by sewing at least a part of each layer, or providing an irregular surface in each layer so as to fit the irregularities) may also be employable and may be appropriately changed depending on the intended use.

<Properties>

As the visceral model A101 employs the foam layer A20, in incising or dissecting the foam layer (incising or dissecting with a scalpel, a surgical knife, or an energy device (such as cautery knife)), a bubble portion gives moderate changes of feeling and generates a specific sense of dissection in the layer.

In addition, when the visceral model A101 is configured to have a laminate structure, in exfoliation of the layers (for example, exfoliation of the foam layer A20 from the first layer A10, exfoliation of the foam layer A20 from the third layer A30, or exfoliation of the first layer A10 from the third layer A30 (rapture inside the foam layer A20)), the foam portion is raptured as being torn off, so that it is possible to exhibit properties similar to actual exfoliation of real objects (real viscera).

In a case where an existing visceral model (a visceral model including a hydrogel) is incised with an energy device (such as a cautery knife), contact between the tip of the energy device (the tip of the cautery knife) and the solid content of the hydrogel may cause scorch. In the present invention, employing the foam structure reduces the solid component content (volume %) with respect to the volume of the foam layer A20 while maintaining the solid component content (mass %) with respect to the mass of the foam layer A20 (it is possible to reduce an amount of solid component per unit volume of the layer (bulk density) while maintaining the solid component content (mass %) in the layer as per usual). Accordingly, the problem of scorch caused by using the energy device can be solved without impairing the texture of the layer.

Furthermore, in an existing visceral model (particularly, a visceral model including a physically cross-linked hydrogel), when the model is incised with an energy device (such as a cautery knife), water sometimes flows out excessively as the hydrogel is incised and melts. In particular, when the layer is colored, there are some cases that the flowing water remains around a portion to be incised and hinders an operative field.

However, in the present invention, since the foam structure is employed in the foam layer A20, even when the water content (mass %) with respect to the mass of the foam layer A20 is maintained or increased, it is possible to reduce the water content (volume %) with respect to the volume of the foam layer A20 (it is possible to reduce an amount of water per unit volume of the layer (bulk density) while maintaining the water content (mass %) in the layer as per usual to hold the texture). Accordingly, it is also possible to reduce the outflow of water to an appropriate level at the time of incision with an energy device without impairing the texture of the layer (it is possible to suppress unnecessary outflow of water even when there is no choice but to increase the water content with respect to the mass of the layer in order to obtain a specific texture).

Furthermore, when the foam layer A20 is subjected to localized injection (localized injection: injection of a liquid (pharmaceutical or the like) by a needle or the like), the foam layer A20 has a property of moderate swelling as seen in real objects (real viscera). Although the detailed principle of this property is unknown, it is assumed that the property of swelling attributes to the foam structure (for example, (1) when a liquid is injected into the foam layer A20, the foam layer A20 is deformed in a unique manner (entering of liquid into the bubble portion, a deformation of the bubble portion while being crushed, or the like), and (2) the foam layer A20 relatively reduces the density and easily causes deformation).

<Use>

According to the visceral model of the present invention, due to its various properties as described above, the visceral model may be used for simulations of various types of surgeries and various kinds of sites of interest with one visceral model, and, the visceral model is suitable for, for example, simulations of dissection (specifically, the term "dissection" is actions of dissection, division, incision, or resection of various tissues (for example, tissues around viscera such as peritoneum, fat layer, stratum disjunctum, and synechia)). Particularly, since the visceral model has the aforementioned properties, it is suitable for simulations of incision and dissection with a surgical energy device (such as a cautery knife, an ultrasonic knife, and a high frequency radio wave knife) and for a simulation of localized injection. Examples of more specific use of the visceral model according to the present invention include various types of surgical simulations such as cholecystectomy, prostate nerve-sparing surgery, per oral endoscopic myotomy (POEM), endoscopic full-thickness resection (EFTR), and dissection (for example, lymph node dissection). In addition, the visceral model according to the present invention is also suitable for a simulation of endoscopic submucosal dissection (ESD) which is recently performed in surgeries of sites such as esophagus, stomach, and large intestine.

As an example of the specific use of the visceral model A101, a case where the visceral model A101 is used for a simulation of ESD will hereinafter be described with reference to FIG. 5. Hereinafter, the visceral model A101 will be illustrated as a gastric model having the structure illustrated in FIG. 1C (that is, a four-layer structure having the first layer A10, foam layer A20, third layer A30, and fourth layer A40) (in this case, with regard to a correspondence relationship between the visceral model A101 and each layer in the stomach, the first layer A10 corresponds to a mucosa layer, the foam layer A20 corresponds to a submucosa layer, the third layer A30 corresponds to a particular muscular layer, and the fourth layer A40 corresponds to a tumor).

Figure 5:
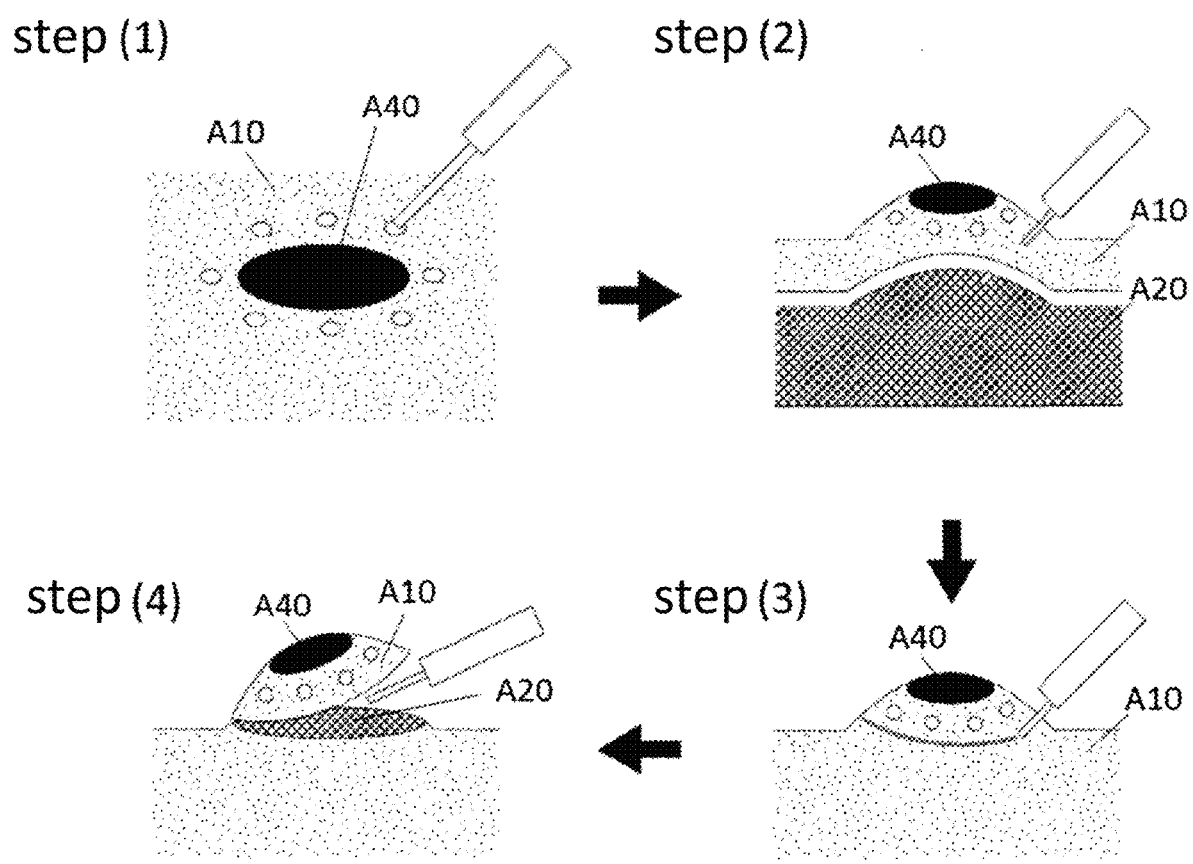
FIG. 5 illustrates conceptual diagrams, shown as steps (1) to (4), illustrating an exemplary use of the visceral model A101 according to the present embodiment.

First, as illustrated in step (1) of FIG. 5, the mucosa layer (the first layer A10) is marked in order to clarify the range in which the tumor (the fourth layer A40) is resected. Next, as illustrated in step (2) of FIG. 5, a pharmaceutical is injected into the submucosa layer (the foam layer A20) to float the tumor (the fourth layer A40) together with the mucosa layer (the first layer A10). Next, as illustrated in step (3) of FIG. 5, the mucosa layer (first layer A10) is incised by a cautery knife or the like so as to surround the portion marked. Next, as illustrated in step (4) of FIG. 5, the tumor (the fourth layer A40) is resected together with the submucous layer (the foam layer A20) by the cautery knife or the like.

ESD is an alternative to the conventional endoscopic mucosal resection (EMR), promising the radical cure, since lesions can be collectively removed by ESD with high efficiency. However, ESD requires a high degree of skill, compared to EMR. Since the visceral model according to the present invention has a texture and a feeling resembling much closer to a real object (real viscera), the visceral model has a beneficial effect on acquisition of a high degree of skill requiring complicated and delicate work.

The visceral model A101 according to this embodiment is applicable to all viscera by changing its laminate structure, being usable as a visceral model of lung, heart, chest wall, abdominal wall, diaphragm, gallbladder, stomach (inner wall), liver, kidney, bladder (inner wall), or skin and the like. It is also possible to use the visceral model A101 as a model that resembles a specific tissue in a certain viscus (for example, submucosa layer of the stomach).

Furthermore, by appropriately changing the shape of the visceral model A101, the visceral model A101 can be used as a tubular visceral model resembling, for example, blood vessel, esophagus, stomach (hollow), small intestine, large intestine, bile duct, pancreatic duct, bladder (hollow), ureter, urethra, vagina, anus, or portal vein and the like.

Hereinafter a visceral model in which the shape of the visceral model A101 (the foam layer A10) is changed to a tubular shape is described.

<<Modification>>

A visceral model according to a modification (hereinafter referred to as a "visceral model B101") includes a foam layer having a tubular shape (hollow shape). With regard to the structure, production method, and the like of the visceral model B101, differences from those in the present embodiment will hereinafter be described. For example, the material, and use of the visceral model B101 are the same as described above, so that the explanation thereof will be omitted.

<Structure>

The visceral model B101 is a hollow visceral model including a laminate in which a plurality of layers is laminated in a tubular shape (a tubular shape when viewing a cross section in a laminating direction). The cross-sectional tubular shape is not particularly limited, and any shapes may be employable as long as they are a closed surface with any straight lines and/or curved lines, and the cross-sectional tubular shape may be appropriately changed to circular, elliptical, or polygonal shapes depending on the intended use.

Figure 6A:
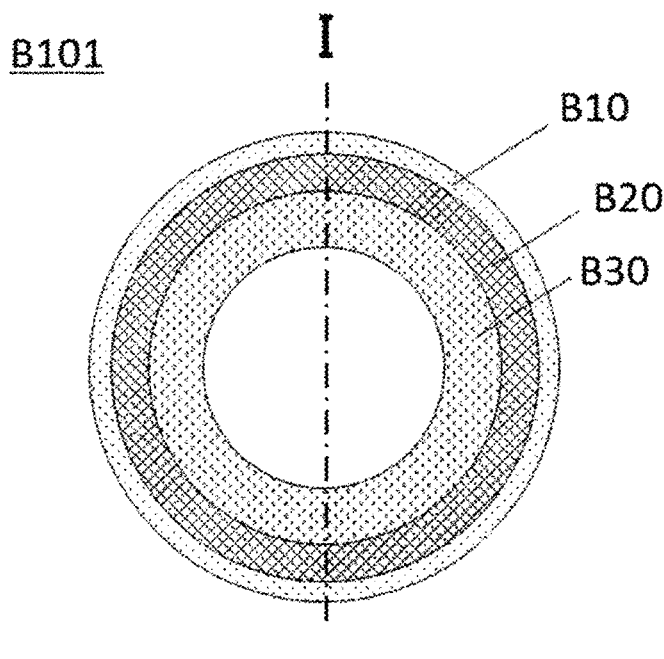
FIGS. 6A and 6B illustrate conceptual diagrams of a visceral model B101 according to a modification.
Figure 6B:
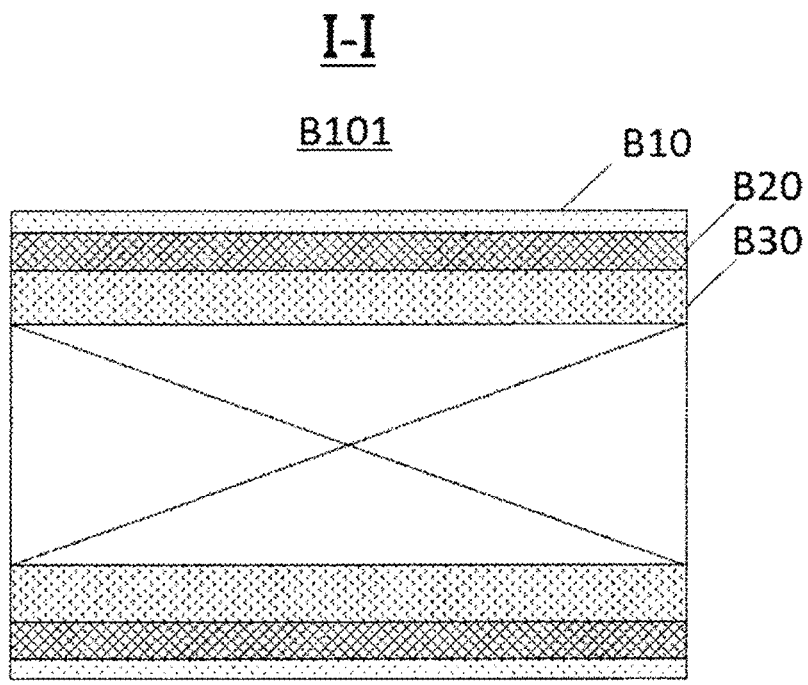

More specifically, as illustrated in FIGS. 6A and 6B, the visceral model B101 has a laminate structure, including a second layer B20 which is a foam layer having a tubular structure (hereinafter referred to as a "foam layer B20"); a third layer B30 provided on one surface (close to the center) of the second layer B20; and a first layer B10 provided on the other surface (close to the periphery) of the second layer B20. As similar to the visceral model A101, the layer structure of the visceral model B101 may be changed appropriately depending on the intended use.

Figure 7A:
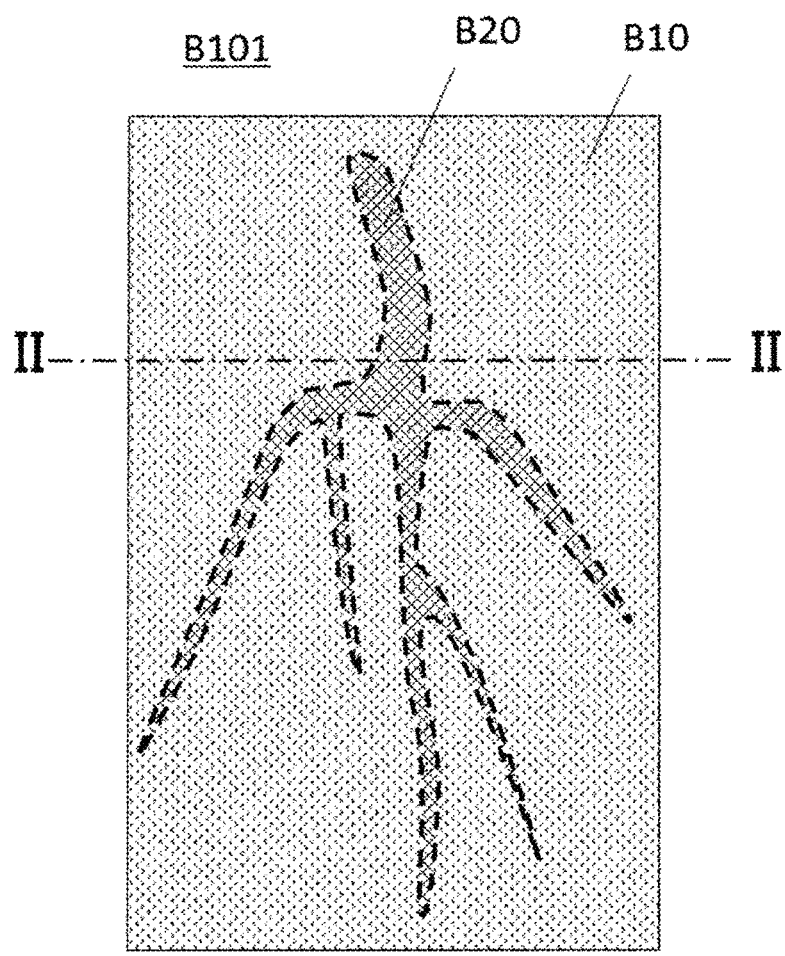
FIGS. 7A and 7B illustrate conceptual diagrams of the visceral model B101 according to the modification.
Figure 7B:
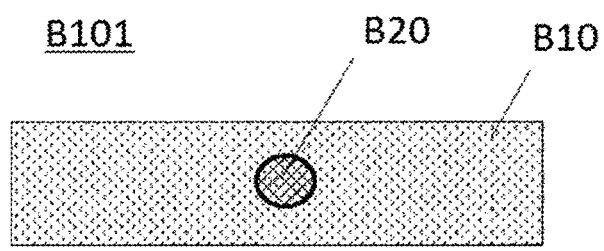

Although the visceral model B101 is illustrated as a hollow cylindrical visceral model, it can be appropriately changed depending on the intended use, and the visceral model B101 may have a structure including a solid foam layer. For example, as illustrated in FIGS. 7A and 7B, the visceral model B101 may have a structure including the first layer B10, and the foam layer B20 formed in an elongated solid tubular (branched) shape and including at least a part buried in or fixed to the first layer (in such a structure, the visceral model is suitable for use as a model of blood vessel and the like). Such a visceral model B101 can be taken as having a laminate structure that includes the second layer B20 which is the foam layer having a tubular (solid) structure, and the first layer B10 which is the layer provided on one surface (close to the peripheral) of the second layer B20.

In the present invention, the visceral model may include a foam layer containing a hydrogel. Therefore, even in the modification, by referring to the description of the present embodiment, the layer structure (for example, the number of laminated layers, or whether to form each layer as a foam layer or a non-foam layer) may be appropriately changed (for example, in the visceral model B101, both of the foam layer B20 and the first layer B10 may be foam layers as illustrated in FIG. 7) depending on the intended use.

<Production Method>

A production method of such a visceral model B101 is not particularly limited and may be produced by known methods. For example, the hollow visceral model B101 may be produced by referring to the method disclosed in JP 5759055 B1 and the like, and as part of the material, a material composition foamed as in this embodiment (foam material) may be used.

EXAMPLES

Hereinafter, the present invention will be described in more detail with reference to Examples and Comparative Example, but the present invention is not limited by these examples.

<<Visceral Model>>

A visceral model according to Examples is the visceral model having the three-layer structure illustrated in FIG. 1A (the visceral model including the first layer A10 to the third layer A30). In Examples, each layer is colored appropriately so that the layers are visually observed easily. In Example, each layer was prepared to have the following thickness: 0.05 to 0.5 mm in the first layer; 0.5 to 5.0 mm in the second layer; and 0.5 to 5.0 mm in the third layer.

Example 1

As shown in Table 1, PVA and water were placed in a beaker and heated at 100° C. for 4 hours with a mantle heater to obtain a solution. Next, the solution and a polysaccharide were mixed, transferred to a metallic container, placed in a freezer at −20° C., and allowed to stand for 10 hours, thereby yielding the first layer (third layer) which is a non-foam layer.

Next, as shown in Table 2, PVA and water were placed in a beaker and heated at 100° C. for 4 hours with the mantle heater to obtain a solution. Next, the solution, a polysaccharide, and a cross-linking agent were mixed to obtain a mixture.

Next, the mixture obtained was subjected to mechanical foaming by air so as to treble a foaming ratio after solidification, thereby yielding a foam material.

Next, the third layer was laid in a metallic container, and the foam material was uniformly spread on the third layer. The foam material was then covered with the first layer, allowed to stand at room temperature for 10 hours, and solidified so as to obtain a model according to Example 1 including the second layer which is the foam layer.

Figure 8:
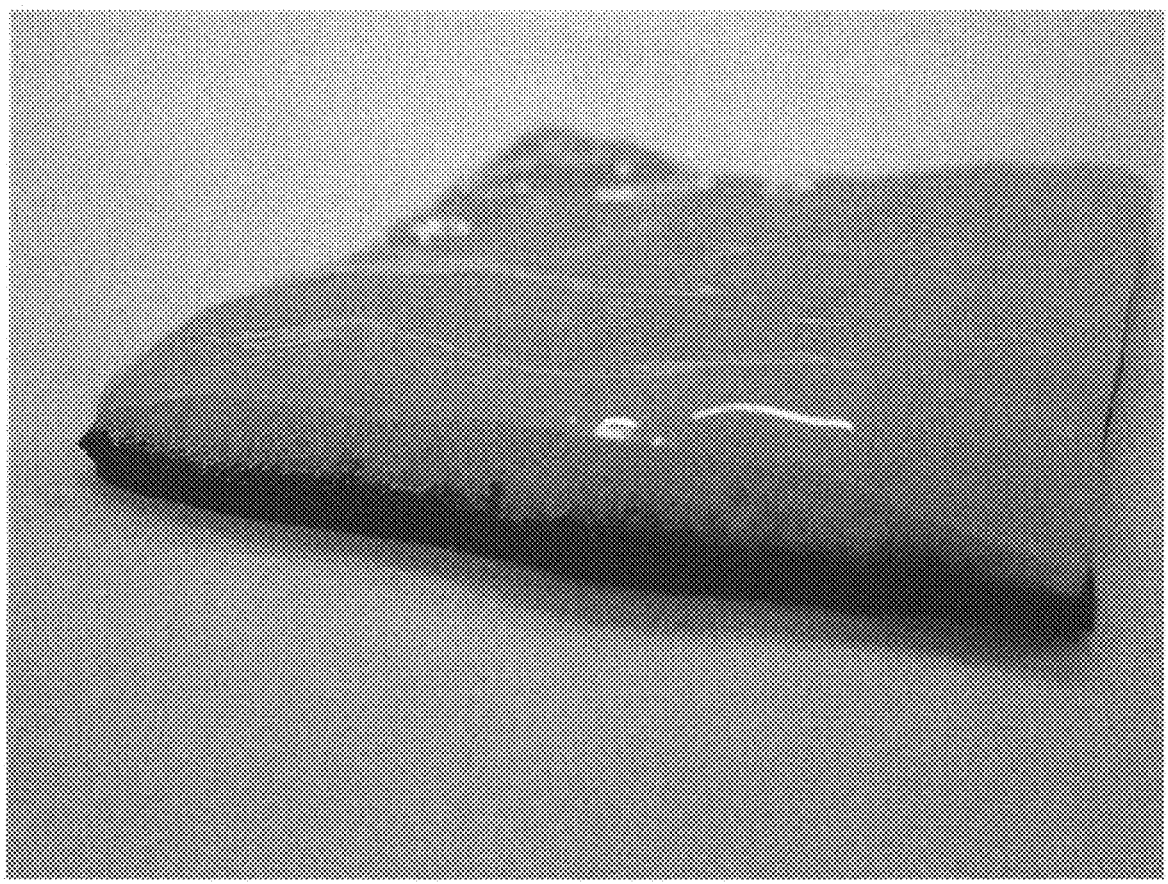
FIG. 8 is a photograph of a visceral model according to Example.

The appearance of the visceral model obtained is shown in the photograph of FIG. 8.

Example 2

As shown in Table 1, PVA and water were placed in a beaker and heated at 100° C. for 4 hours with a mantle heater to obtain a solution. Next, the solution and a polysaccharide were mixed, transferred to a metallic container, placed in a freezer at −20° C., and allowed to stand for 10 hours, thereby yielding the first layer (third layer) which is a non-foam layer.

Next, as shown in Table 1, PVA and water were placed in a beaker and heated at 100° C. for 4 hours with a mantle heater to obtain a solution. Next, the solution and a polysaccharide were mixed to obtain a mixture.

Next, the mixture obtained was subjected to mechanical foaming by air so as to treble a foaming ratio after solidification, thereby yielding a foam material.

Next, the third layer was laid in a metallic container, and the foam material was uniformly spread on the third layer. The foam material was then covered with the first layer, placed in a freezer at −20° C., allowed to stand 10 hours, and solidified so as to obtain a model according to Example 2 including the second layer which is the foam layer.

Comparative Example

A visceral model according to Comparative Example was obtained in a manner similar to Example 2 except that the second layer was not used as a foam layer (the mixture was not foamed).

TABLE 1

| | Material | Amount to be Compounded (parts by mass) |
|---|---|---|
| PVA | Degree of saponification 98.6 (mol %) Degree of polymerization 1600 | 10.0 |
| Polysaccharide | Sodium alginate | 0.50 |
| | Water | 90.0 |

TABLE 2

| | Material | Amount to be Compounded (parts by mass) |
|---|---|---|
| PVA | Degree of saponification 98.4 (mol %) Degree of polymerization 1750 | 9.9 |
| | Cross-linking agent | 0.45 |
| Polysaccharide | Sodium alginate | 0.5 |
| | Water | 90.0 |

<<Evaluation>>

Figure 9A:
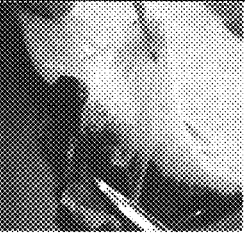
FIGS. 9A to 9C show photographs of visceral models according to Example and Comparative Example at the time of evaluation.
Figure 9B:
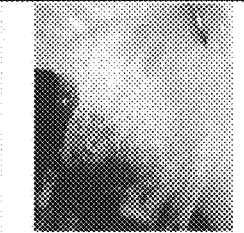
Figure 9C:
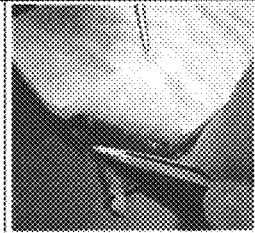

Next, the visceral models according to Examples and Comparative Example were evaluated. Table 3 shows each evaluation result, and FIGS. 9A to 9C show the photographs in each evaluation.

<Evaluation on Texture>

To evaluate the texture of each visceral model, a sense of dissection, appearance, and localized injection were evaluated.

(Evaluation on Sense of Dissection and Appearance)

Each layer was dissected to evaluate a degree of replication in regard to the sense of dissection (a feeling and aspect of ripping tissues while stretching the tissues). A layer that replicated a sufficient sense of dissection was evaluated as ○, and a layer that did not replicate a sufficient sense of dissection or a layer that replicated no sense of dissection was evaluated as x.

(Evaluation on Localized Injection)

The second layer of each visceral model was locally injected (physiological saline, 4 ml) so as to evaluate the degree of replication in regard to a sense of swelling at the time of localized injection. A layer that replicated the sense of swelling was evaluated as ○, and a layer that did not replicate the sense of swelling or a layer that did not swell at all was evaluated as x.

<Characteristics Relative to Cautery Knife>

Next, to evaluate characteristics of each visceral model when using a cautery knife (produced by Osada Medical, Electrosurgery ES-2) as an energy device, scorch and outflow of water were evaluated. In this evaluation, lump layers (foam layer and non-foam layer) produced according to the production method of each Example and Comparative Example were separately prepared and evaluated.

(Evaluation on Scorch)

A degree of scorch was evaluated by visual observation when the cautery knife (condition: monopolar, incision mode, 30 W) was pressed against each layer (foam layer and non-foam layer). A layer with no scorch or a layer with a little scorch was evaluated as ○, and a layer with much scorch was evaluated as x.

(Evaluation on Outflow of Water)

A degree of outflow of water was evaluated by visual observation when the cautery knife (condition: monopolar, incision mode, 30 W) was pressed against each layer (foam layer and non-foam layer). A layer without excessive outflow of water was evaluated as ○, and a layer with excessive outflow of water was evaluated as x.

TABLE 3

| Evaluation item | Example 1 | Example 2 | Comparative Example |
|---|---|---|---|
| Texture | | | |
| Sense of dissection and appearance | ○ | ○ | x |
| Localized injection Characteristics relative to cautery knife | ○ | ○ | x |
| Scorch | ○ | ○ | x |
| Outflow | — | ○ | ○ |

REFERENCE SIGNS LIST

A101, B101 Visceral model
A10, B10 First layer
A20, B20 Second layer (foam layer)
A30, B30 Third layer
A40 Fourth layer
A51, A52 Adhesive

The invention claimed is:

1. A model of viscera, tissues, or organs comprising a foam layer containing a hydrogel,
   wherein a water content of the hydrogel is 50 mass % or more with respect to the entire foam layer,
   wherein the foam layer has an open-cell foam structure, and
   wherein a foaming ratio of the foam layer is 1.1 to 10.0 times.

2. The model of viscera, tissues, or organs according to claim 1, wherein the foam layer contains a polysaccharide.

3. The model of viscera, tissues, or organs according to claim 2, wherein the hydrogel is a polyvinyl alcohol gel.

4. The model of viscera, tissues, or organs according to claim 1, wherein the model is for a simulation of dissection.

5. The model of viscera, tissues, or organs according to claim 1, wherein the model is for a simulation of localized injection.

6. The model of viscera, tissues, or organs according to claim 1, wherein the model is for incision and/or dissection with an energy device.

7. The model of viscera, tissues, or organs according to claim 3, further comprising another layer laminated on one surface of the foam layer, wherein the model is a laminate.

8. The model of viscera, tissues, or organs according to claim 7, further comprising another layer laminated on the other surface of the foam layer.

9. The model of viscera, tissues, or organs according to claim 3, wherein a mean degree of polymerization of the polyvinyl alcohol is 500 to 3000.

10. The model of viscera, tissues, or organs according to claim 3, wherein a degree of saponification of the polyvinyl alcohol is 90 mol % or more.

11. The model of viscera, tissues, or organs according to claim 1, wherein the model has a shape resembling fat layer, mucosa layer, or stratum disjunctum.

12. The model of viscera, tissues, or organs according to claim 1, wherein the model has a shape resembling lung, heart, chest wall, abdominal wall, diaphragm, gallbladder, inner wall of stomach, liver, kidney, bladder of inner wall, or skin.

13. The model of viscera, tissues, or organs according to claim 1, wherein the model is a tubular visceral model having a shape resembling blood vessel, esophagus, stomach (hollow), small intestine, large intestine, bile duct, pancreatic duct, bladder (hollow), ureter, urethra, vagina, anus, or portal vein.

* * * * *